US007905997B2

(12) United States Patent
Groll et al.

(10) Patent No.: US 7,905,997 B2
(45) Date of Patent: Mar. 15, 2011

(54) METHODS AND DEVICES FOR CONTROLLING THE IMPACT OF SHORT CIRCUIT FAULTS ON CO-PLANAR ELECTROCHEMICAL SENSORS

(75) Inventors: Henning Groll, Indianapolis, IN (US); David W. Burke, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 978 days.

(21) Appl. No.: 11/423,797

(22) Filed: Jun. 13, 2006

(65) Prior Publication Data

US 2006/0278538 A1      Dec. 14, 2006

Related U.S. Application Data

(60) Provisional application No. 60/690,284, filed on Jun. 14, 2005.

(51) Int. Cl.
  *G01N 27/327* (2006.01)
(52) U.S. Cl. .................... 204/403.02; 204/401; 324/523
(58) Field of Classification Search ................ 204/401, 204/403.01, 403.02; 205/777.5, 792; 324/523, 324/525
See application file for complete search history.

(56) References Cited

U.S. PATENT DOCUMENTS

| 5,164,747 | A | * | 11/1992 | Osada et al. | ................... 347/19 |
| 5,282,950 | A | | 2/1994 | Dietze et al. | |
| 5,438,271 | A | * | 8/1995 | White et al. | ................. 324/444 |
| 5,711,868 | A | | 1/1998 | Maley et al. | |
| 5,741,634 | A | * | 4/1998 | Nozoe et al. | ............. 204/403.03 |
| 6,743,635 | B2 | * | 6/2004 | Neel et al. | ....................... 436/95 |
| 2004/0194302 | A1 | | 10/2004 | Bhullar et al. | |

FOREIGN PATENT DOCUMENTS

EP     0471986 A2    2/1992

OTHER PUBLICATIONS

PCT Search Report mailed Oct. 23, 2006 from PCT/EP2006/005611 (corresponding application).

* cited by examiner

*Primary Examiner* — Kaj K Olsen
(74) *Attorney, Agent, or Firm* — Justin L. Sage; Roche Diagnostics Operations, Inc.

(57) ABSTRACT

Methods and devices are provided for controlling the impact of undesirable short circuits between non-adjacent but critically matched pairs of electrodes in a co-planar electrochemical sensor. In one embodiment, the size and/or shape of at least one electrode is configured to induce a short circuit between electrode pairs for which connectivity is pre-set to be measured by a meter in order to indicate a short circuit between a different pair for which such connectivity is not pre-set to be measured. In another embodiment, the surface area of one or more electrodes, other than the working electrode, which are designed to be exposed to a sample fluid is significantly limited in relation to the surface area of the working electrode that is exposed to the sample fluid.

3 Claims, 7 Drawing Sheets

METHODS AND DEVICES FOR CONTROLLING THE IMPACT OF SHORT CIRCUIT FAULTS ON CO-PLANAR ELECTROCHEMICAL SENSORS

REFERENCE TO RELATED APPLICATION

The present application is based on and claims priority to U.S. Provisional Patent Application No. 60/690,284 filed Jun. 14, 2005, which is hereby incorporated by reference in its entirely.

TECHNICAL FIELD

The present inventions relates to analyte sensors, particularly to electrochemical biosensors for measuring concentration of an analyte in a fluid sample, and more particularly to such electrochemical biosensors having co-planar, multiple electrode systems.

BACKGROUND

In electrochemical sensors having co-planar electrode configurations, unintentional electrical shorts between electrodes can lead to inaccurate estimation or calculation of an amount of an analyte in a sample fluid. Typically this is avoided by conducting certain failsafe system checks on the sensor, such as by the analytical device (meter) to which the sensor corresponds. Common checks include measuring continuity between pairs of electrodes where unintentional shorts can cause inaccurate measurement results. If continuity between electrodes is detected or measured by the circuitry of the meter when such continuity should not exist, the meter displays an error signal and the strip is not used.

Advances in electrochemical sensors, however, have resulted in more complex electrode systems, often comprising three, four, five, even up to between ten and fifteen different electrodes. While measuring continuity between various pairs of electrodes in a system of two, three or even four electrodes can be simple and easy to implement, more complex multiple electrode systems would require much more complex meter programming, including algorithms and/or logic statements and rules. As a result, this simple failsafe may be less practicable to implement.

One particularly undesirable short circuit in a co-planar electrochemical sensor is between a working electrode and any other electrode that may come in contact with a fluid sample applied to the sensor. Typically, the electrochemical response of the analyte in the fluid sample is proportional to the surface area of the working electrode in contact with the sample. In certain sensors, such as capillary channel fill sensors, one or more sample sufficiency electrodes may be provided in a downstream location in order to detect a sufficient fill level of the sample in the sample channel. If one or more such sufficiency electrodes is shorted to the working electrode, then the working electrode's surface area is effectively increased by the amount of the sufficiency electrode in contact with the fluid sample. Relatively accurate estimation or calculation of the concentration of the targeted analyte depends in part on a generally constant value of working electrode surface area through which the current generated from the predetermined reaction flows. Thus, the increased working electrode surface area that is caused by the undesirable short circuit produces a higher concentration measurement result.

It is generally known, for example in a Therasense Frestyle electrochemical sensor, to provide any other electrodes that come in contact with the fluid sample with generally smaller surface areas than the working electrode. In the past, however, this is done only in sensors comprising a facing (or opposing) electrode configuration. Generally, the intent of such a design is to provide a large counter electrode that does not limit the current induced by the electrochemical reaction at the working electrode, and to assure that the sample chamber of the electrochemical sensor is completely filled before a measurement sequence is initiated. Incidentally, it is as a result of the facing configuration that there is a reduced likelihood of undesirable shorts, and the probability of a harmful short circuit is much less in the facing configuration.

SUMMARY OF THE INVENTION

It is against the above background that the present invention provides certain unobvious advantages and advancements over the prior art. In particular, the inventor has recognized a need for improvements in methods and devices for controlling the impact of short circuit faults on co-planar electrochemical sensors.

Although the present invention is not limited to specific advantages or functionality, it is noted that the present invention provides various embodiments for limiting the effect on the analyte measurement of short circuit faults between a working electrode and any other electrode that is intended, by design, to come in contact with the sample fluid. Two exemplary ways of doing this are disclosed herein, namely providing an electrode configuration that induces an otherwise undetected short circuit between one or more pairs of electrodes which the system is already configured to detect and minimizing the surface area of such other electrodes that contact sample fluid in relation to the surface area of the working electrode.

In accordance with one embodiment of the present invention, an electrochemical sensor is provided for measuring the concentration of an analyte in a sample fluid. The sensor is adapted for being received by and electrically connected to a meter, and it comprises a co-planar electrode system having a working electrode, a plurality of other electrodes and a sample receiving area. First and second electrodes of such other electrodes are configured each to be electrically isolated from the other and from the working electrode. The first electrode comprises a distal end at least a portion of which is exposed within the sample receiving area. The second electrode has at least one end configured to extend substantially between the working electrode and the first electrode proximate the one end. As a result, an undesired electrical connectivity between the working electrode and the first electrode must also result in electrical connectivity between the first electrode and the second electrode proximate the one end.

In accordance with other embodiments, the meter is configured to verify the electrical isolation between the working electrode and the second electrode and between the first electrode and the second electrode when the sensor is electricity connected to the meter, but it is not configured to verity the electrical isolation between the working electrode and the first electrode.

In accordance with yet other embodiments, a method is provided for indirectly verifying electrical isolation between non-adjacent electrodes of an electrochemical sensor having a co-planar electrode system. The method comprises the steps of providing a working electrode and at least first and second electrodes on the sensor, at least a portion of the working electrode and the first electrode being exposed in a sample receiving area of the sensor, the second electrode being provided having at least one end configured to extend substantially between the working electrode and the first electrode proximate the one end, each of the first electrode, second electrode and working electrode being intended to be electrically isolated each from the other; inserting the sensor into a meter configured to receive and electrically connect with the sensor; using the meter to detect or measure electrical connectivity between the working electrode and the second electrode; using the meter to detect or measure electrical connectivity between the first electrode and the second electrode; and displaying an error message on the meter if electrical connectivity is detected or measured between the working electrode and the second electrode or between the first electrode and the second electrode. With this method, any undesired electrical connectivity between the first electrode and the working electrodes must also result in electrical connectivity between the first electrode and the second electrode proximate the one end of the second electrode.

In accordance with yet other embodiments, an electrochemical sensor is provided for measuring concentration of an analyte in a sample fluid. The sensor is adapted for being received and electrically connected to a meter, the sensor comprising a co-planar electrode system having a sample receiving area, a working electrode at least a portion of which is exposed within the receiving area, and at east one other electrode, the at least one other electrode being configured to be electrically isolated from the working electrode and comprising a distal end at least a portion of which is exposed within the sample receiving area, the surface area of the exposed portion of the at least one other electrode being no more than about 50% of the surface area of the exposed portion of the working electrode.

In accordance with yet other embodiment at method is provided for controlling the affect of a short circuit between critically matched electrodes in an electrochemical sensor having a co-planar electrode system. The method comprises the steps of providing an electrochemical sensor having a sample receiving area, a working electrode having at least a portion exposed within the sample receiving area, and at least one other electrode intended to be electrically isolated from the working electrode and comprising a distal end having at least a portion thereof exposed within the sample receiving area; providing the at least one other electrode with a surface area of the exposed portion of the distal end thereof being no more than about 50% of these surface area of the exposed portion of the working electrode.

These and other features and advantages of the present invention will be more fully understood from the following detailed description of the invention taken together with the accompanying claims. It is noted that the scope of the claims is defined by the recitations therein and not by the specific discussions of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.

DETAILED DESCRIPTION OF THE INVENTION

In order that the invention may be more readily understood, reference is made to the following examples, which are intended to illustrate the invention, but not limit the scope thereof.

It is noted that terms like "preferably", "commonly", and "typically" are not utilized herein to limit the scope of the claimed invention or to imply that certain features are critical, essential, or even important to the structure or function of the claimed invention. Rather these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a qualitative representation may vary from a stated reference without resulting in a change in the basic function of the subject matter at issue.

Figure 1:
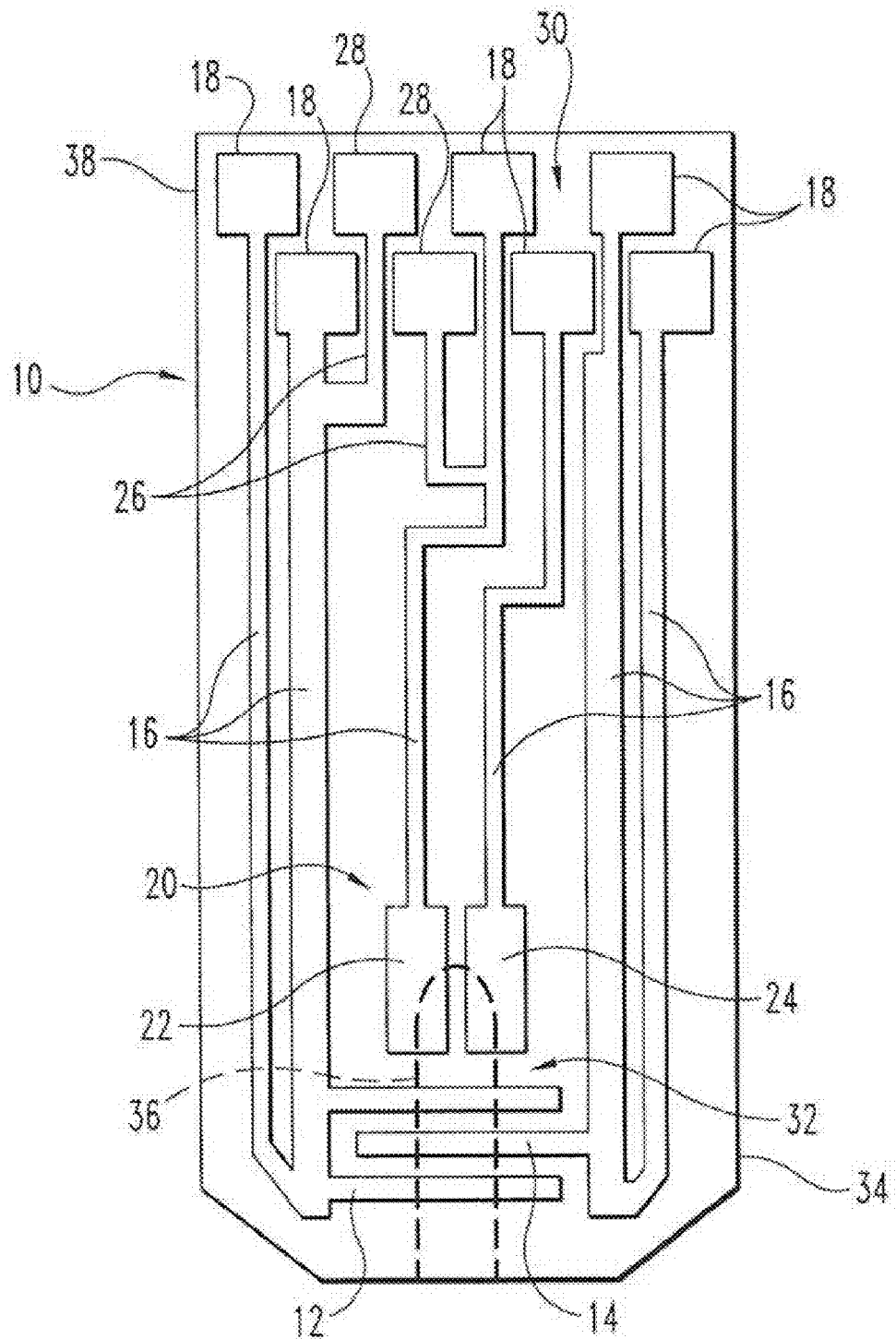
FIG. 1 is a top view of a prior art embodiment of the insertion end of a sensor having a complex multiple electrode system.
Figure 2:
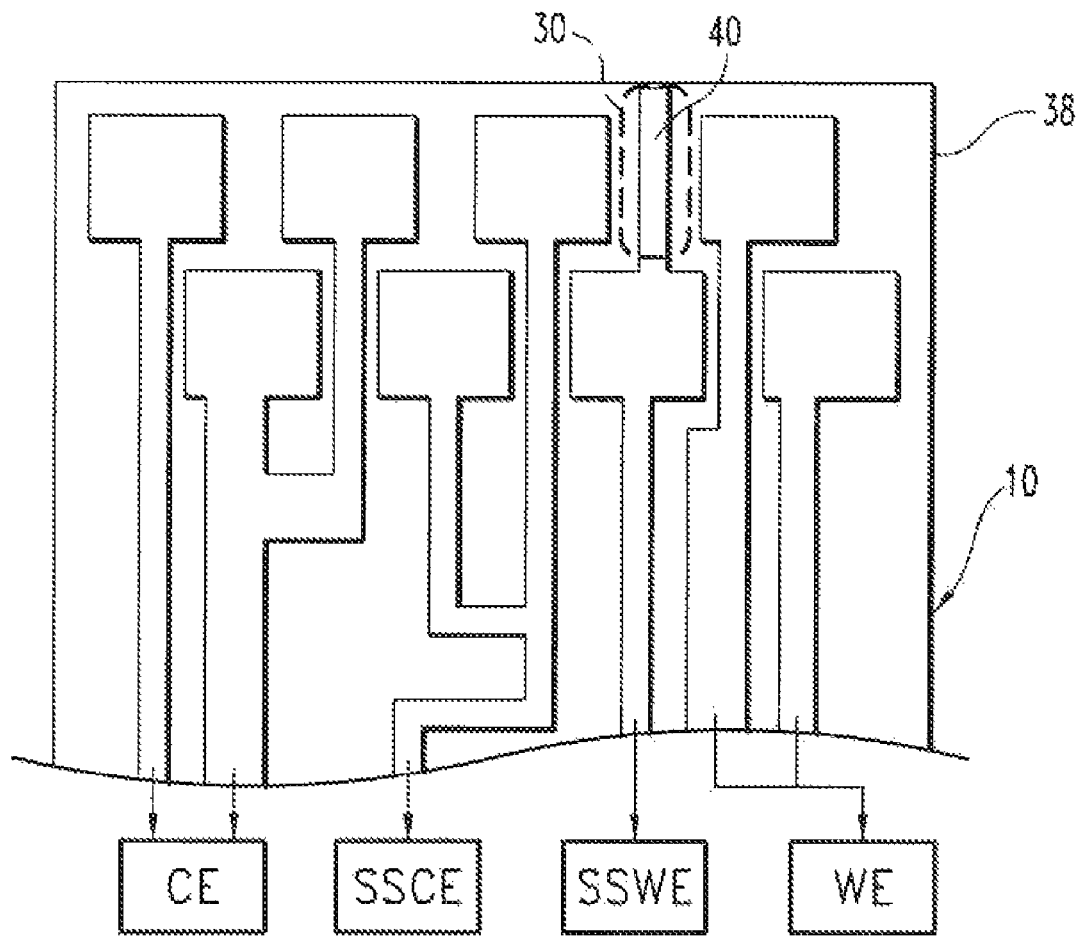
FIG. 2 is a top view of the insertion end of a sensor according to an alternative embodiment of the present invention providing at least one electrode with a size and/or shape configured to induce a detectable short circuit between adjacent electrodes in order to indicate a short circuit between non-adjacent electrodes.
Figure 3:
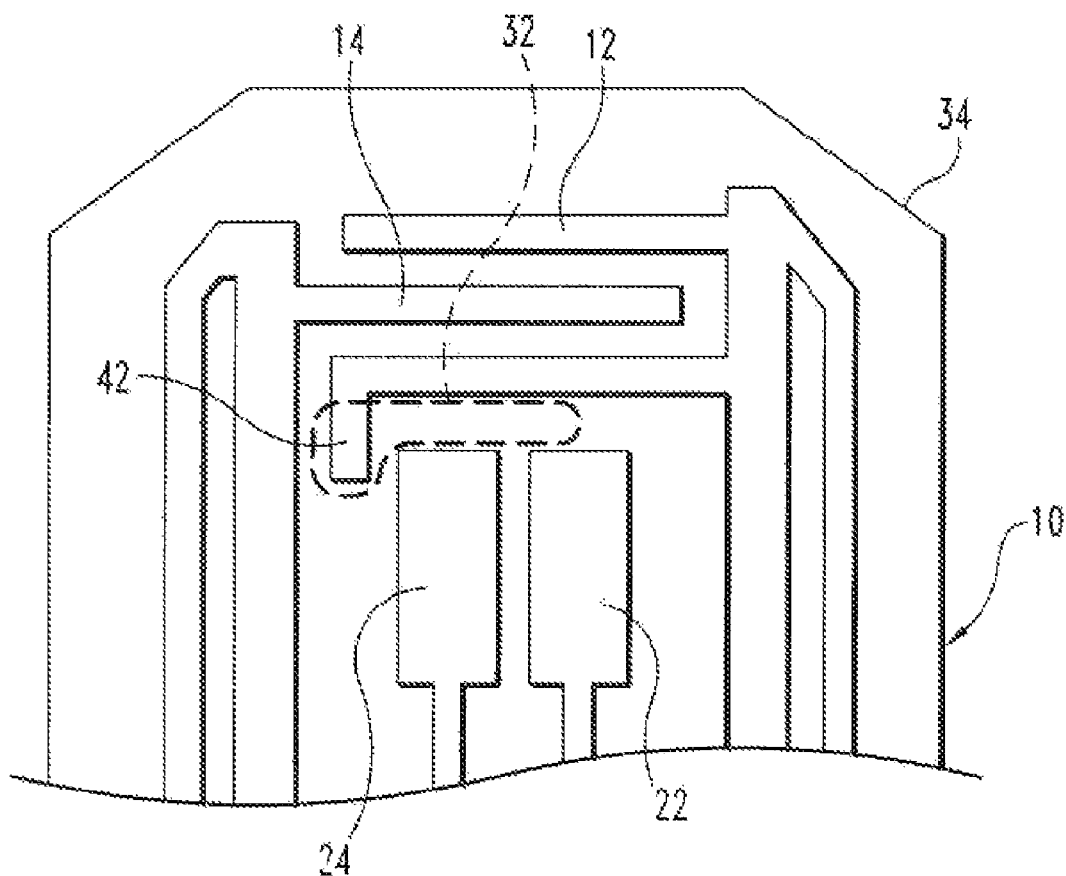
FIG. 3 is a top view of the sample-channel end of a sensor according to another alternative embodiment of the present invention providing at least one electrode with a size and/or shape configured to induce a detectable short circuit between critically matched electrodes in order to indicate a short circuit between non-adjacent electrodes.

Referring now to FIGS. 1-3, electrochemical sensors 10 may be provided with complex electrode systems. For example, from FIG. 1, each of the counter and working electrodes 12, 14 (herein referred to as "CE" and "WE" respectively) in one embodiment of such a sensor comprise dual trace leads 164 with independent contact pads 18 for electrically connecting the electrodes 12, 14 to a meter (not shown). Sample sufficiency electrodes 20 may also be provided, for example the sample sufficiency counter electrode 22 and sample sufficiency working electrode 24 (hereinafter referred to as "SSCE" and "SSWE" respectively). Furthermore, additional, auxiliary trace leads 26 and their respective contacts 28 may be provided in electrical connection with the trace lead 16 for one or more of the electrodes 12, 14 provided on the sensor 10. The purposes and configurations for each of these components are known to Applicants, but not relevant to the current disclosure. As a result, no further discussion regarding the specific configurations and purposes of the various electrode components will be described herein, except as such may relate to the present invention.

Complex electrode systems provided on a relatively small sensor 10 give rise to certain space constraints. For example, as shown in FIG. 1, the contact pads 18, 28 in one embodiment are staggered in at least two lateral rows. Each laterally-adjacent contact pad in this staggered configuration pertains to every other trace lead provided in the electrode system; thus, adjacent tracer leads do not extend into laterally-adjacent contact pads. For example, the trace lead 16 for the WE 14 is adjacent the trace lead 16 for the SSWE 24, but the contact pad 18 for the WE 14 is laterally adjacent the contact pad 18 for the SSCE 22 whereas the contact pad 18 for the SSWE 24 is laterally adjacent the trace leads 16 for the SSCE 22 on one side and for the WE 12 on the other.

Except for the connection of the auxiliary trace leads 26 according to a particular electrode system design (for example, as sown in FIG. 1) and except for the dual trace leads of the WE and CE 14, 12, the components of the electrode system are intended to be generally electrically isolated from each other. It is a familiar failsafe to ensure electrical isolation in such systems by using a meter into which the sensor inserted to apply an electrical potential or other electrical effect at the contact pads of a pair of such isolated electrodes, and detecting or measuring electrical effects indicative of electrical connectivity, such as current, potential or resistance, across the critically paired electrodes. Electrical isolation can be absolute (e.g. infinite resistance or zero current), or can be subjective predetermined (e.g. a threshold minimum resistance or threshold maximum current). (For purposes of this disclosure and the scope of the claims, the term "measuring" is intended and used to refer to any detection (as against absolute isolation) of an electrical effect indicative of connectivity as well as any quantification (for comparison against a predetermined threshold) thereof. Whether electrical isolation is desired to be absolute or subject to an allowable threshold is within the direction of the person practicing the invention and is not a limitation of the scope of the invention.) If after applying a potential or other electrical effect, electrical isolation cannot be confirmed or verified, an error message is provided and the sensor is not permitted to be used.

Due to the complexity of certain electrode systems, such as in FIG. 1, or due to the fixed design and methodology of a meter with which such an electrode system is intended to be used, it may be difficult or cost-ineffective to provide or modify a meter to perform this failsafe on each and every pair of electrode contact pads that are intended to be electrically isolated. Furthermore interposition of certain components of the system, such as the contact pad and trace lead of the SSWE 24 being located generally between the trace leads of the SSCE 22 and the WE 14, makes undesirable shorts unlikely to be missed, provided that the electrodes with adjacent lead traces 16 are checked against each other, such as the SSCE 22 and SSWE 24, or the SSWE 24 and the WE 14. Thus, the meter-sensor system may rely on certain strategic failsafe checks to account for all possible failsafe modes.

Although not highly likely, there remains the possibility that a short can occur between electrodes which are not checked this way because their relative locations make such shorts difficult. For example, for the sensor at FIG. 1, SSCE 22 and WE 14 may be left unchecked due to the interposition of the contact pad and trace lead of the SSWE 24, the SSWE 24 being separately checked by the meter for isolation from the SSCE 22 and the WE 14. However, the space 30 above the contact pad for the SSWE 24 and between the contact pad for the SSCE 22 and WE 14 is left open. Due to any number reasons, such as manufacturing defects, it remains possible that the SSCE 22 and WE 14 could be shorted together across this open space 30. Similarly, an open trail 32 can be identified at the sample channel end 34 of the sensor 10 between the SSCE 22 and the trace lead of the WE 14.

Despite the unlikelihood of an undesired short circuit occurring across either of these location 30, 32, the fact that it is not impossible may present significant problems with the accuracy of the analyte measurement results provided by the meter. As discussed above, if the WE 14 is shorted to another electrode that is exposed in the sample channel 36 such that such other electrode comes into contact with the sample fluid (not shown), the practical effect is that the surface area of the WE 14 is increased by the amount of exposed surface area of the other electrode. The measured current increases accordingly, which provides a high bias to calculations that are dependent upon a constant surface area for the WE 14.

From the configuration of the sensor of FIG. 1, this could occur if either of the SSWE 24 or SSCE 22 are shorted to any part of the WE 14 because the SSWE 24 and SSCE 22 are included in the sample channel 36 for purposes of the sample sufficiency detection functionality. To maintain a relatively simple meter set up, the meter failsafe checks may check SSWE 24 against SSCE 22 (necessary in order for the sample sufficiency functionality to work properly) and SSWE 24 against WE 14 (because they are mostly adjacent and more likely to face undesirable shorting). As pointed out above, there remains the slight possibility of shorting the SSCE 22 to the WE 14 across the open space 30 at the contact pad end 38 and the open trail 32 at the sample channel end 34.

Referring now to FIGS. 2 and 3, the size and/or shape of certain aspects of the electrodes may be configured to prevent this possibility. From FIG. 2, the contact pad of the SSWE 24 can be provided with an extension 40 toward the contact pad end 38 of the sensor 10 to interrupt the open space 30. As a result, any cause of a short across the open area 30 likely induces a short between the SSWE 24 and the WE 14, for which a failsafe is provided, due to the space constraints. Even if the short would not have otherwise spanned across the entire open space 30, the extension 40 from the contact pad of the SSWE 24 ensures that any possible short in that space 30 also will at least cause a short either between the SSCE 22 and SSWE 24 or between the SSWE 24 and WE 14, if not both.

Similarly, from FIG. 3, the open trail 32 may be interrupted by a portion 42 of the CE extending into the trail. As a result, any cause of a short that would otherwise course over the open trail 32 will induce a short between the CE 12 and WE 14, for which a failsafe is already provided.

Figure 4:
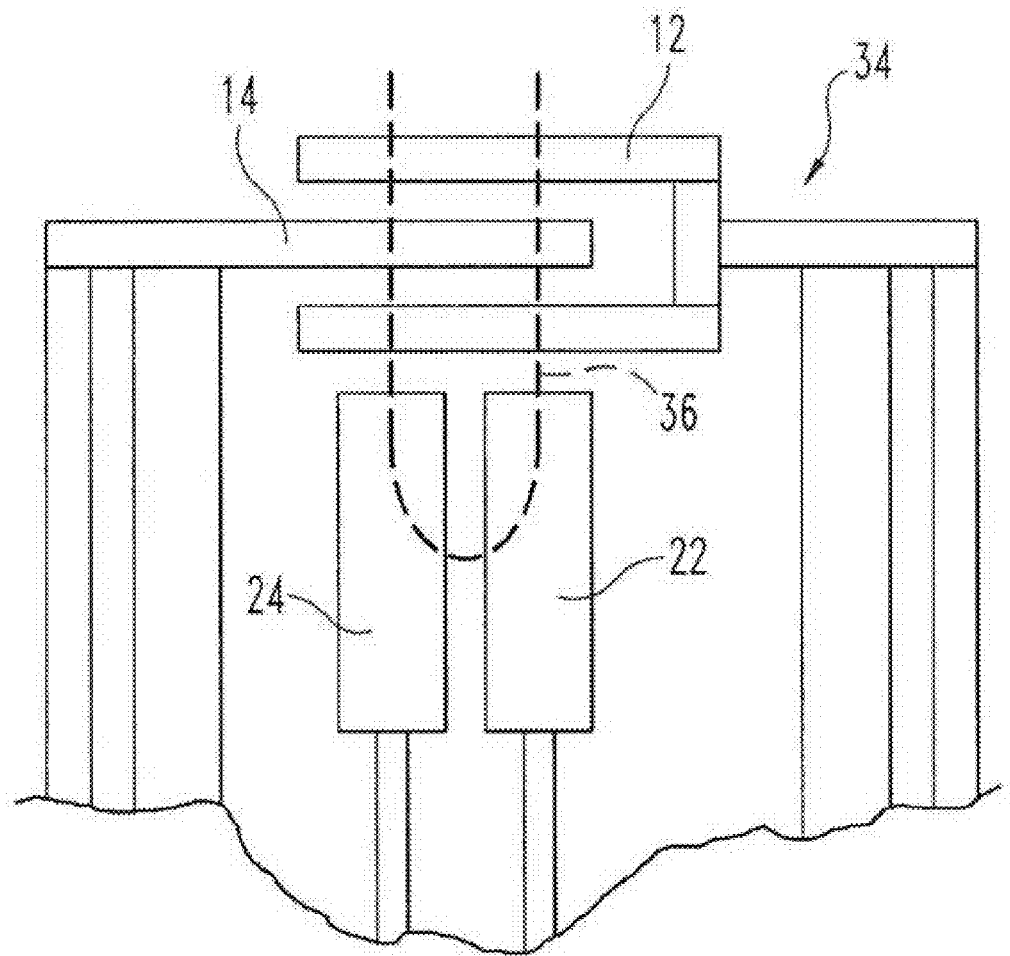
FIG. 4 is a top view of a prior art embodiment of the sample-channel end of a sensor having a complex multiple electrode system.
Figure 5:
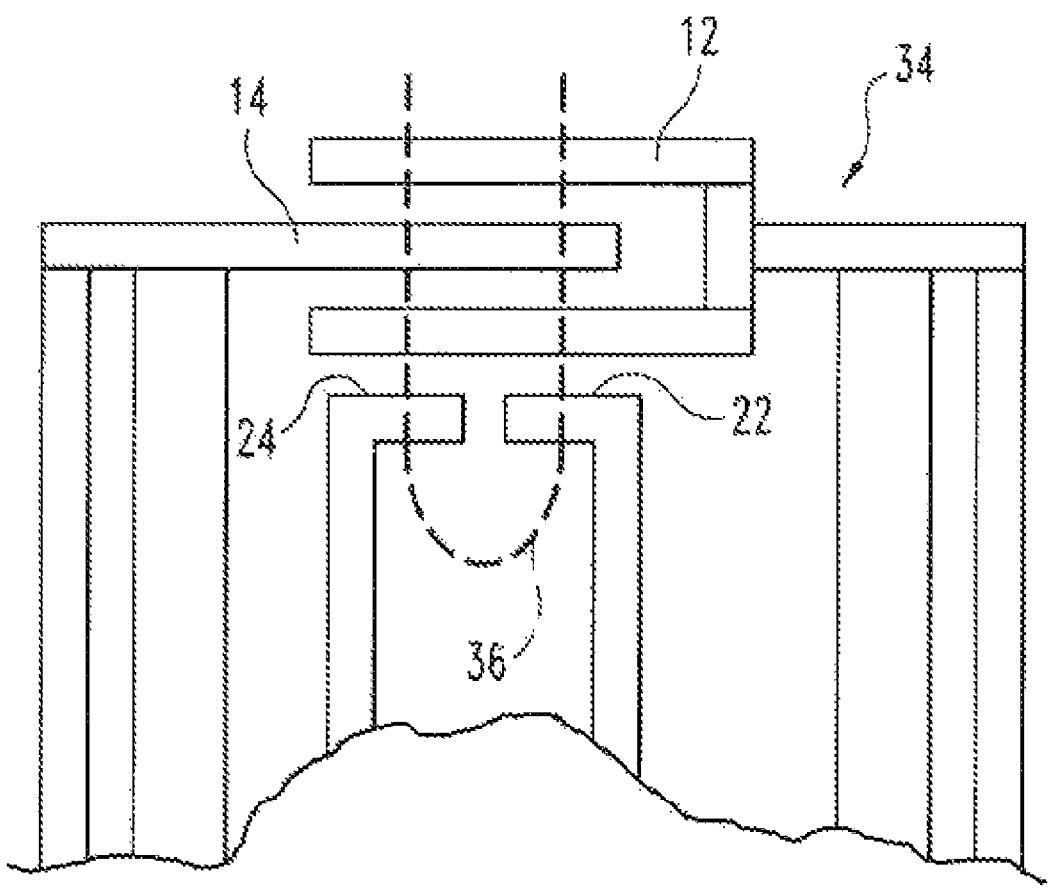
FIG. 5 is a top view of the sample-channel end of a sensor according to one embodiment of the present invention providing sample-sufficiency electrodes of significantly reduced surface area exposed in the sample channel.

As indicated the result of undesirable shorts between the WE 14 and other electrodes that are exposed by design in the sample channel 36 is a high bias to the measurement result caused by an increased effective surface area for the WE 14. Referring now to FIGS. 4-7, an alternative embodiment of the present invention at least minimizes the resulting high bias to an acceptable level. FIG. 4 shows a prior art configuration of the sample channel end 34 of a sensor 10, in which the SSCE 22 and SSWE 24 are exposed in the sample channel 36 for purposes of detecting fluid sample (not shown) filling the channel up to that point, downstream from the portions of the CE 12 and WE 14 exposed in the channel 36. In FIG. 4, the exposed surface area of each of the SSCE 22 and SSWE 24 is less than the exposed surface area of the WE 14, but significantly more than about 50% of the exposed WE 14. A short between the WE 14 and any of the SSCE 22 and SSWE 24 would thus increase the effective surface area by at least about 60-70% or more.

To minimize the undesirable effects of this increase, embodiments of the present invention limit the exposed surface area of the SSCE 22 and SSWE 24 in the sample channel 36 to no more than about 50% of the exposed surface area of the WE 14 in the sample channel 36. In other embodiments the exposed surface area of the SSCE 22 and SSWE 24 in the sample channel 36 is limited to no more than about 10% of the exposed surface area of the WE 14 in the sample channel 36.

Various configuration for reduced SSWE 24 and SSCE 22 surface area can be implemented, including various sizes and shapes for the exposed portions thereof. For example, in FIG. 5 (not shown to scale), the trace leads for the SSCE 22 and SSWE 24 extend down the sensor 10 so as to straddle the sample channel 36 and extend therein perpendicularly from opposite sides so that they are laterally aligned. In such embodiments, the electrodes 22, 24 extend only partially into the channel 36 in order to minimized exposed surface area within the sample channel.

Figure 6:
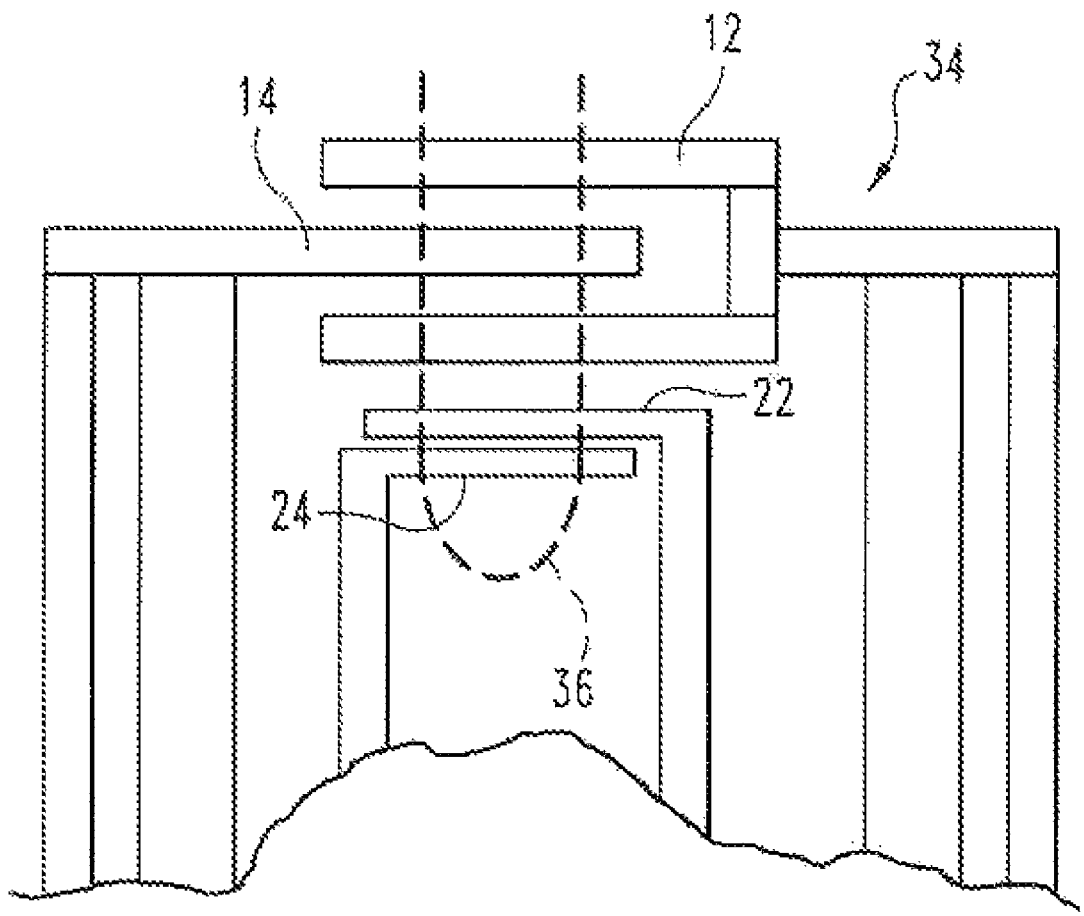
FIG. 6 is a top view of the sample-channel end of a sensor according to another embodiment of the present invention providing sample-sufficiency electrodes of significantly reduced surface area exposed in the sample channel.

In the embodiment of FIG. 6 (not shown to scale), the trace leads for the SSCE 22 and SSWE 24 extend down the sensor 10 similarly straddling the channel 36, and extend therein perpendicularly, but offset linearly so that each electrode 22, 24 may extend substantially across the channel 36. In such embodiments, the electrodes 22, 24 are typically narrower (thinner) in order to minimize exposed surface area within the sample channel 36.

Figure 7:
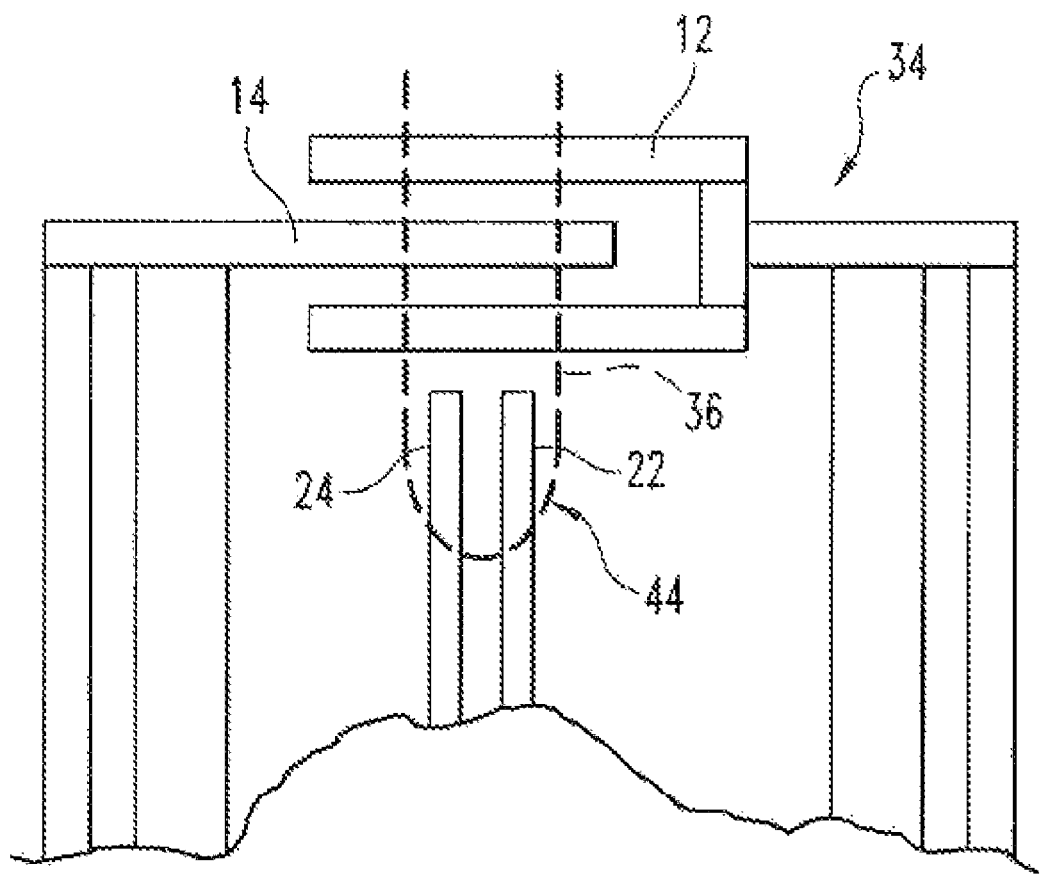
FIG. 7 is a top view of the sample-channel end of a sensor according to yet another embodiment of the present invention providing sample-sufficiency electrodes of significantly reduced surface area exposed in the sample-channel.

In the embodiment of FIG. 7 (not shown to scale), the trace leads of the SSCE 22 and SSWE 24 extend down the sensor 10 generally directly into the proximal end 44 of the sample channel 36 to a point short of the CE 12. In such embodiments, the electrodes 22, 24 are again narrower (thinner) in order to minimize exposed surface area within the sample channel 36.

In addition to the foregoing embodiments pertaining to electrode structures on the sensors, the present invention further sets forth embodiments of methods relating to the use of such sensors with a meter configured for receiving and electrically connecting with such sensors. Steps relating to the methods are disclosed in this specifications and recited in the claims appended hereto.

Having described the invention in detail and by reference to specific embodiments thereof, it will be apparent that modifications and variations are possible without departing from the scope of the invention defined in the appended claims. More specifically, although some aspects of the present invention may be identified herein as preferred or particularly advantageous, it is contemplated that the present invention is not necessarily limited to those aspects of the invention.

What is claimed is:

1. An electrochemical sensor for measuring concentration of an analyte in a sample fluid, comprising a co-planar electrode system and a sample receiving area, the electrode system comprising a plurality of electrodes each having a distal end at least partially exposed within the sample receiving area and a proximal end comprising a contact pad, each distal end being connected to a corresponding contact pad by a trace lead extending therebetween, each contact pad being configured for electrical connection to a meter configured for use with the electrochemical sensor; wherein first and second electrodes of the plurality of electrodes have respective contact pads laterally spaced apart with a space between them, a third electrode of the plurality of electrodes being located substantially entirely between the first and second electrodes, the contact pad of the third electrode being located entirely between the respective trace leads of the first and second electrodes, the third electrode further comprising a terminal extension extending from the contact pad thereof into the space between the contact pads of the first and second electrodes.

2. The electrochemical sensor of claim 1, the sensor further comprising a trail located generally between the distal end of the first electrode and the second electrode, wherein a fourth electrode of the plurality of electrodes comprises a second terminal extension extending from the distal end thereof into the trail between the distal end of the first electrode and the second electrode, the second terminal extension extending away from the sample receiving area from a portion of the fourth electrode distal end which is not exposed within the sample receiving area.

3. The sensor of claim 2 wherein at least one of the plurality of electrodes other than the second and third electrodes is disposed substantially between the first electrode and the fourth electrode.

\* \* \* \* \*